United States Patent
Lehrman et al.

(10) Patent No.: US 6,666,830 B1
(45) Date of Patent: Dec. 23, 2003

(54) SYSTEM AND METHOD FOR DETECTING THE ONSET OF AN OBSTRUCTIVE SLEEP APNEA EVENT

(75) Inventors: Michael L. Lehrman, Washington, DC (US); Michael E. Halleck, Longmont, CO (US)

(73) Assignee: East River Ventures, LP, New York, NY (US)

( * ) Notice: Subject to any disclaimer, the term of this patent is extended or adjusted under 35 U.S.C. 154(b) by 0 days.

(21) Appl. No.: 09/641,982

(22) Filed: Aug. 17, 2000

(51) Int. Cl.[7] ............................................... A61B 7/00
(52) U.S. Cl. ....................................... 600/586; 600/529
(58) Field of Search ............................... 600/529, 532, 600/538, 543, 586

(56) References Cited

U.S. PATENT DOCUMENTS

| | | | | |
|---|---|---|---|---|
| 4,715,367 A | * | 12/1987 | Crossley | 600/27 |
| 4,982,738 A | * | 1/1991 | Griebel | 600/483 |
| 5,265,624 A | * | 11/1993 | Bowman | 600/546 |
| 5,295,490 A | * | 3/1994 | Dodakian | 600/534 |
| 5,522,382 A | * | 6/1996 | Sullivan et al. | 600/532 |
| 5,738,102 A | * | 4/1998 | Lemelson | 600/483 |
| 5,879,313 A | * | 3/1999 | Raviv et al. | 600/595 |
| 5,961,447 A | * | 10/1999 | Raviv et al. | 600/300 |
| 5,989,193 A | * | 11/1999 | Sullivan | 600/534 |
| 6,168,568 B1 | * | 1/2001 | Gavriely | 600/529 |
| 6,241,683 B1 | * | 6/2001 | Macklem et al. | 600/529 |
| 6,290,654 B1 | * | 9/2001 | Karakasoglu | 600/529 |

* cited by examiner

Primary Examiner—Charles Marmor

(57) ABSTRACT

There is disclosed a system and method for detecting the onset of an obstructive sleep apnea event before the obstructive sleep apnea event fully develops and before the cessation of breathing occurs. The system comprises one or more microphones capable of detecting breathing sounds within an airway of a person. The microphones generate signals representative of the breathing sounds and send the signals to a controller. The controller identifies at least one signal pattern that is associated with a breathing pattern of the person that occurs at the onset of an obstructive sleep apnea event. The controller may also identify at least one signal pattern that is associated with a partially occluded breathing pattern of the person. The controller identifies the signal patterns by using digital signal processing techniques to analyze the signals representative of breathing sounds. The method involves detecting breathing sounds within an airway of a person, generating signals representative of the breathing sounds, and identifying at least one signal pattern that is associated with a breathing pattern of the person that occurs at the onset of an obstructive sleep apnea event.

25 Claims, 5 Drawing Sheets

SYSTEM AND METHOD FOR DETECTING THE ONSET OF AN OBSTRUCTIVE SLEEP APNEA EVENT

CROSS REFERENCE TO RELATED APPLICATION

The inventors of the present invention have filed a related patent application Ser. No. 09/641,983 concurrently with this application entitled "System and Method for Treating Obstructive Sleep Apnea". The related patent application and the inventions disclosed therein are assigned to the assignee of the present invention and are incorporated herein by reference for all purposes as if fully set forth herein.

TECHNICAL FIELD OF THE INVENTION

The present invention is directed to a system and method for detecting the onset of an obstructive sleep apnea event before cessation of breathing occurs.

BACKGROUND OF THE INVENTION

Apnea is the cessation of breathing. Sleep apnea is the cessation of breathing during sleep. Sleep apnea is a common sleep disorder that affects over twelve million (12,000,000) people in the United States. Persons with sleep apnea may stop and start breathing several times an hour while sleeping. Each individual episode of the cessation of breathing is referred to as a sleep apnea event.

When a person stops breathing during sleep the person's brain soon senses that oxygen levels in the blood are low and carbon dioxide levels in the blood are high. The brain then sends emergency signals to the body to cause the body to try to increase gas exchange in the lungs to increase the amount of oxygen and to decrease the amount of carbon dioxide. The body's autonomic physiological reflexes initiate survival reactions such as gasping for air, the production of enzymes to constrict arteries to increase blood pressure, and the production of enzymes to increase heart rate. The person will then usually gasp for air and thereby restore the effective gas exchange of oxygen and carbon dioxide in the lungs. This causes the sleep apnea event to end.

The brain may also cause the body's autonomic physiological reflexes to release large amounts of adrenaline in order to stir the person to gasp for air. Over a period of time repeated rushes of adrenaline in the body can have negative effects and can lead to heart damage and other medical problems.

Often the person wakes up while gasping for air. Even if the person does not become conscious while gasping for air, the body's sleep state is interrupted and the body is physiologically stressed during each sleep apnea event. Sleep apnea events can occur multiple times during a period of sleep. That is, the process of ceasing to breathe, become physiologically stressed, and gasping for air may be repeated numerous times during a period of sleep. Successive sleep apnea events cause a person to experience many short interrupted periods of sleep.

Interrupted periods of sleep can produce varying levels of fatigue, lack of energy, and daytime sleepiness. Other symptoms may include restless sleep, loud and sometimes heavy snoring, morning headaches, irritability, mood changes, behavior changes, and similar emotional or physical disorders. While mild forms of sleep apnea may exist without apparent harm to the individual, severe cases may lead to such conditions as weight gain, impotency, high blood pressure, stroke, mental problems, memory loss, and even death.

Sometimes sleep apnea directly causes death during sleep due to asphyxiation because of a lack of oxygen. More frequently sleep apnea indirectly causes death because of motor vehicle crashes, job-site accidents, and similar events which are due to sleepiness caused by sleep deprivation.

There are two forms of sleep apnea. The two forms are central sleep apnea and obstructive sleep apnea. At the present time, central sleep apnea and obstructive sleep apnea are thought to originate from two different sources. Central sleep apnea appears to be linked to a malfunction of the brain that interferes with neurological signals that normally control the breathing process. Obstructive sleep apnea is caused by a blockage of the breathing airway that completely stops the flow of air to and from the lungs. A common form of obstructive sleep apnea occurs when fleshy tissue in a sleeping person's throat collapses and seals off the pharyngeal airway. A condition called mixed sleep apnea results when central sleep apnea events and obstructive sleep apnea events alternate.

Sometimes central sleep apnea directly causes death during sleep when the sleeping person completely ceases breathing. Death results from asphyxiation due to a lack of oxygen. More frequently obstructive sleep apnea indirectly causes death because of motor vehicle crashes, job-site accidents, and similar events that are due to sleepiness caused by sleep deprivation.

Because of the variety and degree of symptoms, diagnosis of obstructive sleep apnea typically requires more than a simple analysis of symptoms. Depending upon the symptoms and severity, diagnosis may include a thorough physical exam, an examination of the mouth and throat for abnormalities, and sleep studies. Thorough sleep studies include additional tests such as electrocardiogram (ECG) tests for detecting arrhythmias, and tests for arterial blood gases to find sleep periods in which the blood oxygen level is below its normal low level.

Successful treatment for obstructive sleep apnea must ensure that a person's breathing passages remain open during sleep. The simplest treatments include weight reduction, change in body position while sleeping, avoidance of alcohol, avoidance of sedatives, and similar changes in lifestyle. When anatomical obstructions are found to be the source of obstructive sleep apnea, surgery may be required for removal of enlarged tonsils, enlarged adenoids, excess tissue at the back of the throat, and similar types of obstructions. In more extreme cases, an opening may be created in the trachea in order to bypass the obstruction that is blocking the airway during sleep.

One device for the treatment of obstructive sleep apnea is a device that pumps fresh air into a mask worn over the nose. This device provides what is known as nasal continuous positive airway pressure (CPAP). When the mask and air flow are properly adjusted, the air pressure opens the upper air passage enough to prevent snoring and known forms of apnea. The disadvantages of the CPAP treatment include 1) discomfort and sleep disruption caused by the nose mask and the mechanism for connecting the mask to the air pumping device, and 2) original and on-going cost for the apparatus, and 3) inconvenience when the sleeping location changes. Some newer types of CPAP devices do not use a mask (e.g., the CPAP device disclosed in U.S. Pat. No. 6,012,455).

In addition to the more traditional treatments for obstructive sleep apnea described above, alternatives are constantly being studied and developed. Medications are being researched, but no medication has yet been developed which has proven to be effective. Mechanical devices that are inserted into the mouth while sleeping have been tried with varying success. For instance, devices which keep the jaw or tongue in proper position are sometimes effective in cases where breathing is obstructed by a large tongue or a "set back" jaw. However, these devices have some disadvantages. They are uncomfortable to wear during sleep (which causes them to not be regularly used). Each device must have a different design for each specific type of air passage obstruction. Each device must be individually sized for each patient.

More recently, systems have been developed for the purpose of clearing upper airway passages during sleep using the electrical stimulation of nerves or muscles. In some cases, these systems require surgical implantation of sensors and associated electronics that detect when breathing has ceased and then stimulate the breathing process. Some hybrid systems have been developed that require surgical insertion of one or more sensors plus external equipment for monitoring the breathing process or moving the obstruction when breathing ceases. These systems may produce positive results but they also have associated risks due to surgery, may need replacement at later times (requiring additional surgery), and may have higher costs and lower reliability than the more traditional treatments. In addition, the hybrid systems also have the accompanying physical restrictions and accompanying disadvantages associated with connections to the external equipment.

Therefore, there is a need in the art for an improved system and method for treating obstructive sleep apnea. In particular, there is a need in the art for a system and method that does not create other types of sleep disturbing effects, does not require surgical implementation, and does not have the high costs associated with some of the types of treatments currently in use.

Prior art systems and methods are directed toward detecting and treating an obstructive sleep apnea event after the obstructive sleep apnea event has occurred. It would be very advantageous, however, to be able to detect the onset of an obstructive sleep apnea event before the obstructive sleep apnea event fully develops. That is, if the onset of an obstructive sleep apnea event can be detected before the sleeping patient actually stops breathing, steps can be taken to prevent the obstructive sleep apnea event from occurring.

Therefore, there is a need for a system and method for detecting the onset of an obstructive sleep apnea event before the obstructive sleep apnea event fully develops. In particular, there is a need for a system and method for detecting the onset of an obstructive sleep apnea event before the cessation of breathing occurs.

SUMMARY OF THE INVENTION

The present invention is directed to a system and method for detecting the onset of an obstructive sleep apnea event before the sleep apnea event fully develops into cessation of breathing.

The system of the present invention comprises one or more microphones that are capable of detecting breathing sounds within an airway of a sleeping person. The microphones generate signals that are representative of the detected breathing sounds and transfer the signals to a controller. The controller identifies at least one signal pattern that is associated with a breathing pattern of the person that occurs at the onset of an obstructive sleep apnea event. The controller may also identify at least one signal pattern that is associated with a partially occluded breathing pattern of the person. The controller identifies the signal patterns by using digital signal processing techniques to analyze the signals that are representative of breathing sounds.

It is a primary object of the present invention to provide a system and method for detecting the onset of an obstructive sleep apnea event before the obstructive sleep apnea event fully develops into cessation of breathing.

It is also an object of the present invention to provide a controller that is capable of receiving signals that are representative of breathing sounds of a person and identifying within the signals at least one signal pattern that is associated with a breathing pattern of the person that occurs at the onset of an obstructive sleep apnea event.

It is also an object of the present invention to provide a controller that is capable of receiving signals that are representative of breathing sounds of a person and identifying within the signals at least one signal pattern that is associated with a partially occluded breathing pattern of the person.

It is a further object of the present invention to provide a controller that is capable of sending an alarm signal to a base station when the controller identifies a signal pattern that may indicate the onset of an obstructive sleep apnea event.

It is an object of the present invention to provide a controller that is capable of receiving an airflow detection signal from an airflow sensor to determine the breathing rate of a person who is subject to the onset of an obstructive sleep apnea event.

It is also an object of the present invention to provide a controller that is capable of identifying signal patterns by using digital signal processing techniques to analyze signals that are representative of breathing sounds.

It is a further object of the present invention to provide a method for detecting breathing sounds within an airway of a sleeping person, and generating signals that are representative of the breathing sounds, and identifying within the signals at least one signal pattern that is associated with a breathing pattern of the person that occurs before the onset of an obstructive sleep apnea event.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description, it may be advantageous to set forth definitions of certain words and phrases used throughout this patent document: the terms "include" and "comprise" and derivatives thereof mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware, or software, or some combination of at least two of the same.

It should be noted that the functionality associated with any particular controller may be centralized or distributed, whether locally or remotely. Definitions for certain words and phrases are provided throughout this patent document. Those of ordinary skill in the art should understand that in many, if not most, instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the present invention may be implemented in any suitably modified system for detecting the onset of an obstructive sleep apnea event.

Figure 1:
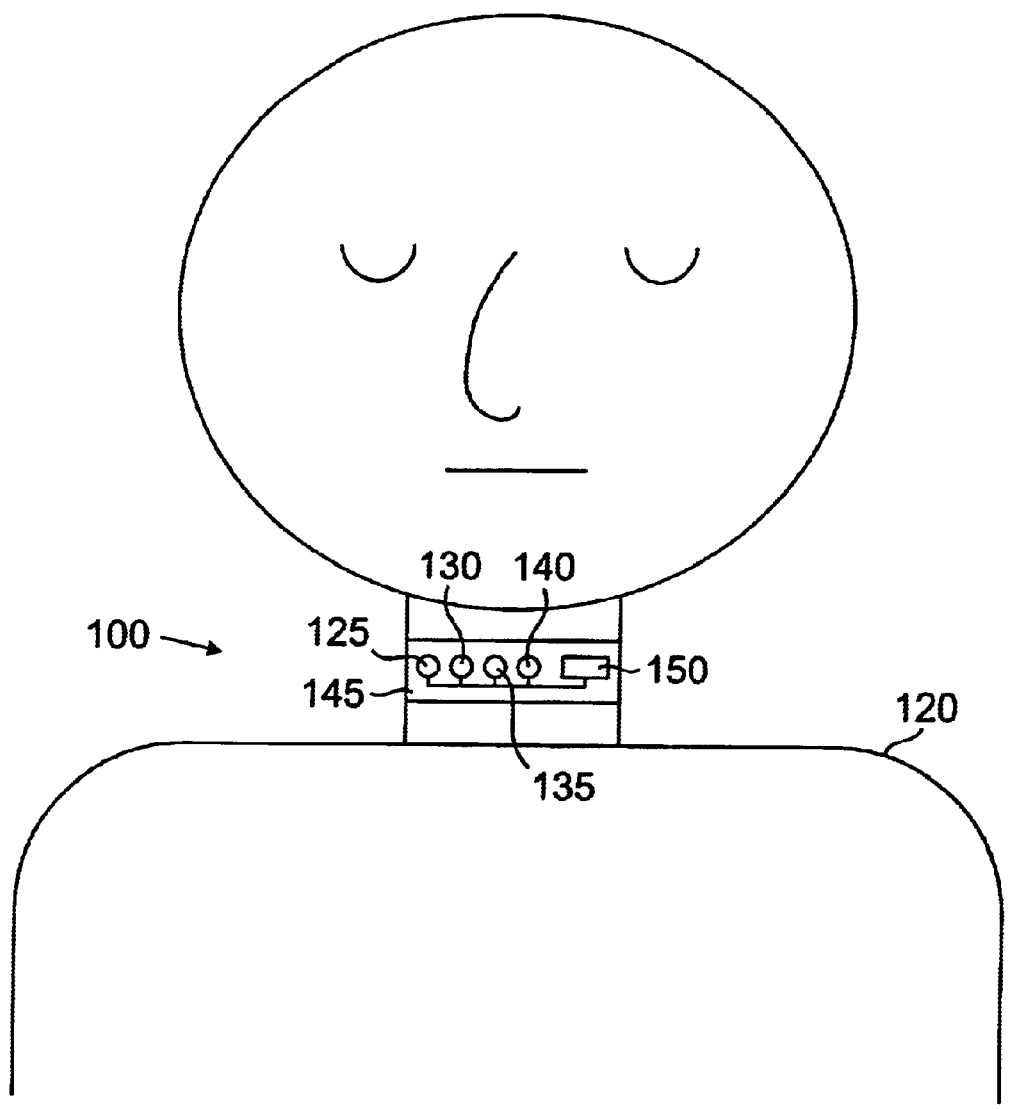
FIG. 1 is diagram illustrating a plurality of microphones and a controller mounted on a collar around the neck of a person whose breathing is being monitored.
Figure 4:
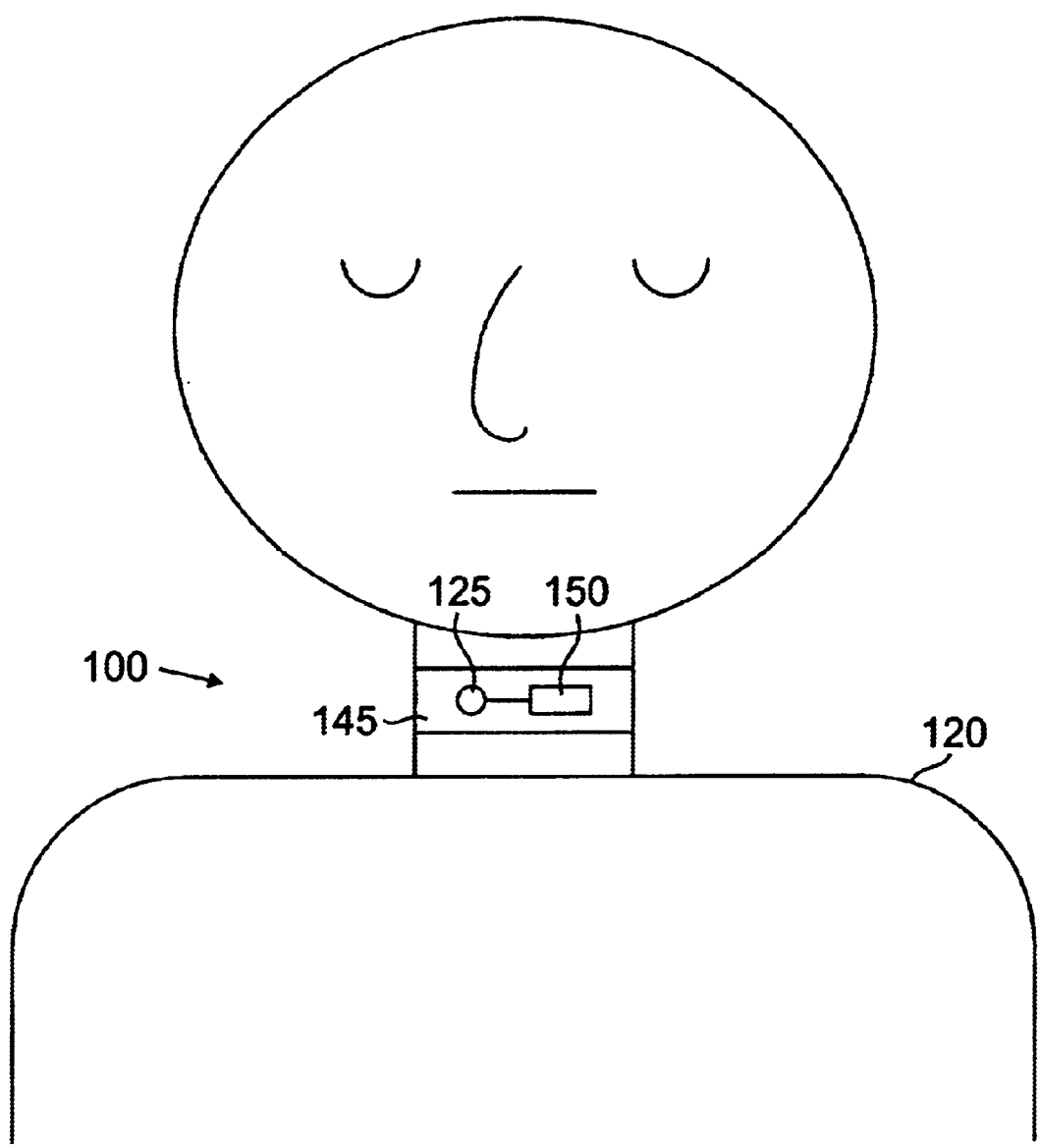
FIG. 4 is a diagram illustrating one microphone and the controller of the present invention mounted on a collar around the neck of a person whose breathing is being monitored.

FIG. 1 illustrates one embodiment of the present invention showing how apparatus 100 of the present invention may be attached to a person 120 who suffers from sleep apnea. Apparatus 100 may comprise either one microphone or a plurality of microphones. The embodiment of the present invention that is illustrated in FIG. 1 has four microphones 125, 130, 135, and 140. It is noted, however, that it is possible to practice the present invention using only one microphone. The embodiment of the present invention that is illustrated in FIG. 4 has only one microphone 125.

Microphones 125, 130, 135, and 140, are each capable of being acoustically associated with person 120. Microphones 125, 130, 135, and 140, are each capable of detecting sounds within a breathing airway of person 120. One type of microphone that is
suitable for use in the present invention is the electret microphone. Microphones 125, 130, 135, and 140, are each attached to collar 145 and collar 145 is detachably fastened around the neck of person 120. Collar 145 may be fastened around the neck of person 120 with a velcro clasp (not shown in FIG. 1) Collar 145 is fastened around the neck of person 120 so that microphones 125, 130, 135, and 140, are positioned adjacent a breathing airway in the neck of person 120.

Each of the microphones 125, 130, 135, and 140, is capable of generating signals representative of the sounds of breathing of person 120. When microphones 125, 130, 135, and 140, detect sounds of breathing, then each microphone generates a signal. The signals generated by each microphone are transferred via an individual microphone signal line to signal processing circuitry 200 (shown in FIG. 2) contained within housing 150.

Figure 2:
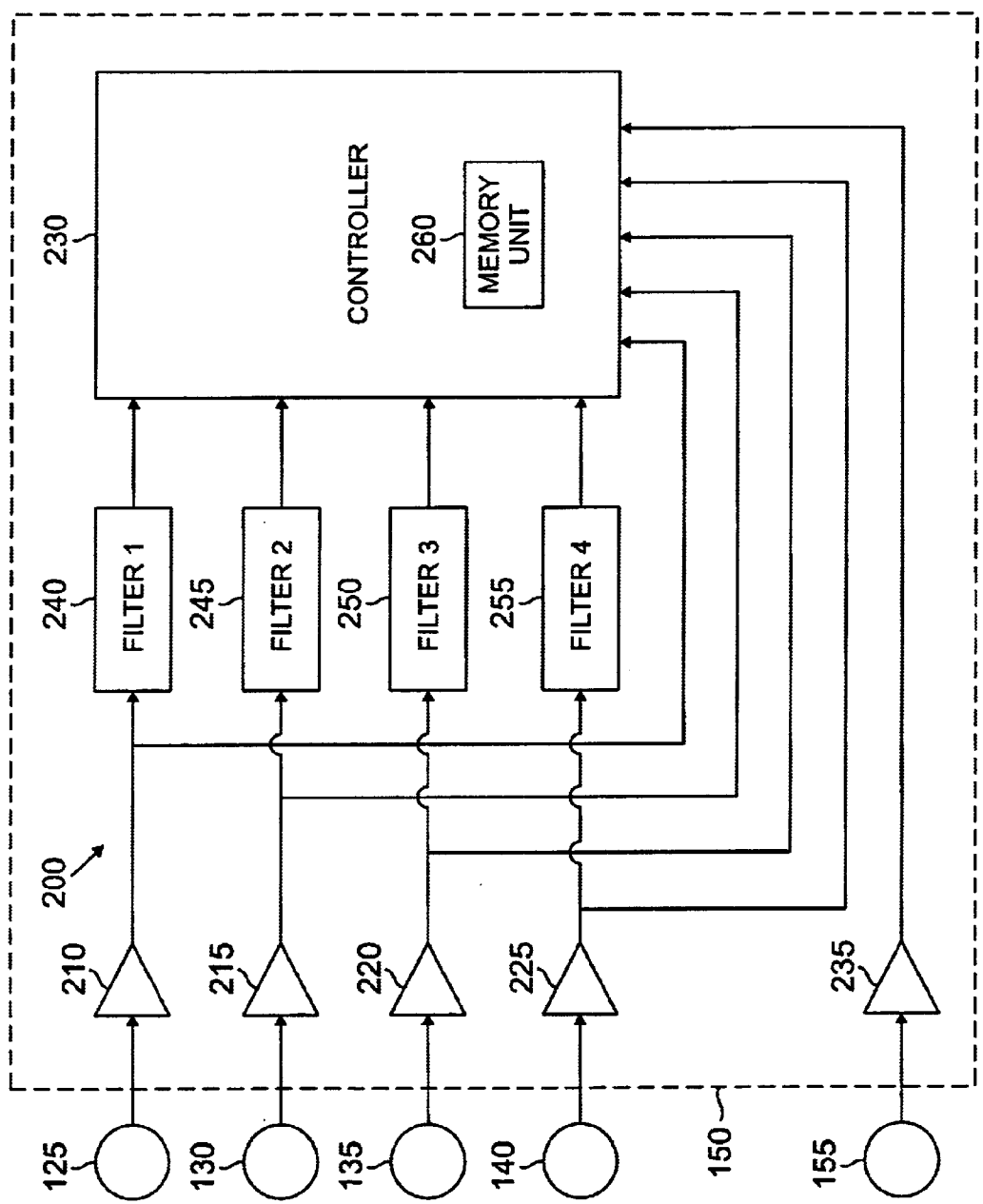
FIG. 2 is a circuit diagram illustrating the connection of the plurality of microphones in FIG. 1 to the controller of the present invention.

Apparatus 100 may optionally be used in conjunction with an airflow sensor 155 (shown schematically in FIG. 2). Airflow sensor 155 is preferably attached near the nostrils of person 120.

Airflow sensor 155 is capable of detecting a flow of air in and out of the nostrils of person 120 and is capable of determining the breathing rate of person 120. Airflow sensor 155 may also be located within other locations in an airway of person 120. Airflow sensors are typically capable of detecting flows of air between frequencies of one tenth Hertz (0.1 Hz) and one and one tenth Hertz (1.1 Hz).

When airflow sensor 155 detects a flow of air, then airflow sensor 155 generates an airflow detection signal. The airflow detection signal generated by airflow sensor 155 is transferred via a signal line to signal processing circuitry 200 (shown in FIG. 2) contained within housing 150. Signal processing circuitry 200 monitors the airflow detection signal of airflow sensor 155 to determine the breathing rate of person 120.

Housing 150 is mounted on collar 145 as shown in FIG. 1. Signal processing circuitry 200 within housing 150 may be connected via signal lines (not shown in FIG. 1) to base station 310 (shown in FIG. 3) located remotely from the site where person 120 is sleeping. In an alternative embodiment, signal processing circuitry 200 may transmit signal information to base station 310 through radio frequency receiver 320 (shown in FIG. 3) using a radio frequency transmitter (not shown) located within housing 150. In another alternative embodiment, signal processing circuitry 200 may transmit signal information to a network site (not shown) such as a site connected to the Internet.

FIG. 2 is a circuit diagram illustrating the connection of microphones 125, 130, 135, and 140, and optional airflow sensor 155 to controller 230 within signal processing circuitry 200. Signals from microphone 125 are transferred to amplifier 210 where the signals are amplified. Similarly, signals from microphone 130 are amplified in amplifier 215, signals from microphone 135 are amplified in amplifier 220, and signals from microphone 140 are amplified in amplifier 225. The amplified signals from amplifiers 210, 215, 220, and 225 are then transferred to controller 230.

Signals from airflow sensor 155 are transferred to amplifier 235 where the signals are amplified. The amplified signals from amplifier 235 are then transferred to controller 230.

Signals from amplifier 210 are also transferred to filter 240 (Filter 1) where the signals are filtered. In one advantageous embodiment filter 240 filters out all signals except signals having frequencies in the range of twenty Hertz (20 Hz) to one hundred Hertz (100 Hz). The filtered signals from filter 240 are then transferred to controller 230.

Similarly, signals from amplifier 215 are also transferred to filter 245 (Filter 2) where the signals are filtered. In one advantageous embodiment filter 245 filters out all signals except signals having frequencies in the range of one hundred Hertz (100 Hz) to one thousand Hertz (1,000 Hz). The filtered signals from filter 245 are then transferred to controller 230.

Similarly, signals from amplifier 220 are also transferred to filter 250 (Filter 3) where the signals are filtered. In one advantageous embodiment filter 250 filters out all signals except signals having frequencies in the range of one thousand Hertz (1,000 Hz) to ten thousand Hertz (10,000 Hz). The filtered signals from filter 250 are then transferred to controller 230.

Lastly, signals from amplifier 225 are also transferred to filter 255 (Filter 4) where the signals are filtered. In one advantageous embodiment filter 250 filters out all signals except signals having frequencies in the range of ten thousand Hertz (10,000 Hz) to twenty thousand Hertz (20,000 Hz). The filtered signals from filter 255 are then transferred to controller 230.

The numerical values given for the frequency ranges are illustrative only. It is clear that other ranges of frequency values may be used to practice the invention.

Controller 230 receives a complete set of filtered and unfiltered signals from microphones 125, 130, 135, and 140. Controller 230 also receives an airflow detection signal from airflow sensor 155. The signals from microphones 125, 130, 135, and. 140 will be collectively referred to as the "microphone signals." As will be more fully explained, controller 230 uses information from the microphone signals to identify a signal pattern that is associated with a breathing pattern of person 120 that occurs at the onset of an obstructive sleep apnea event.

Figure 3:
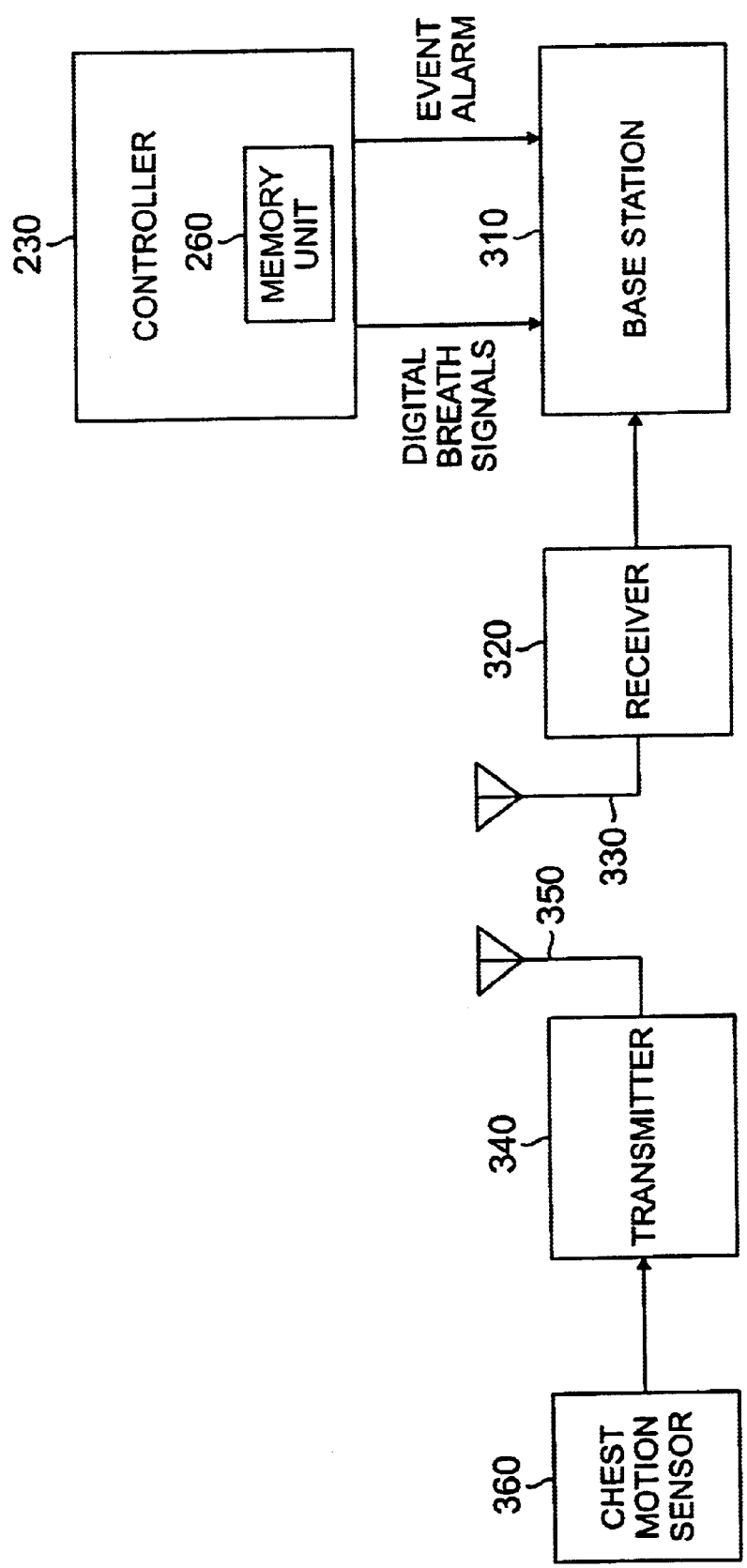
FIG. 3 is a circuit diagram illustrating the connection of the controller of the present invention with a base station and illustrating a communication link between a chest motion sensor and the base station.

As shown in FIG. 3, controller 230 is coupled to base station 310. Controller 230 continually transfers signals to base station 310 concerning the status of the breathing of person 120. An operator of base station 310 can monitor any of the signals within controller 230. Whenever controller 230 identifies a signal pattern that is associated with a breathing pattern of person 120 that occurs at the onset of an obstructive sleep apnea event, controller 230 initiates an obstructive sleep apnea event onset alarm and sends the obstructive sleep apnea event onset alarm to base station 310. Similarly, whenever controller 230 receives no signals from microphones 125, 130, 135, and 140, then controller 230 assumes that person 120 is not breathing. Controller 230 then immediately initiates a "no breathing" alarm and sends the, "no breathing" alarm to base station 310.

Base station 310 is also coupled to radio frequency receiver 320 having receiver antenna 330 for receiving radio frequency transmissions from radio frequency transmitter 340 through transmitter antenna 350. Radio frequency transmitter 340 is coupled to a chest motion sensor 360 that is coupled to the chest of person 120. Chest motion sensor 360 senses the rhythmical motion of the chest of person 120 during breathing. In this manner, radio frequency transmitter 340 continually transfers signals to base station 310 concerning the status of the chest motion of person 120.

Controller 230 comprises software for analyzing the microphone signals. The software in controller 230 utilizes digital signal processing techniques for finding the frequency domain components of each microphone signal. The digital signal processing techniques used by controller 230 may be of any type including, without limitation, Fast Fourier Transform techniques. Controller 230 also comprises memory unit 260 that is capable of storing 1) digital signal processing analysis software for analyzing the microphone signals, and 2) signal patterns that result from the digital signal processing analysis of the microphone signals, and 3) software for comparing signal patterns.

Controller 230 is capable of identifying and storing signal patterns from the microphone signals. For example, when person 120 is breathing normally, controller 230 receives microphone signals that indicate normal breathing. The signal pattern that results from the digital signal processing analysis of the "normal breathing" microphone signals is stored in memory unit 260 as a "normal breathing" signal pattern. Controller 230 is capable of recalling the "normal breathing" signal pattern from memory unit 260 in order to compare other signal patterns with the "normal breathing" signal pattern.

A person who suffers from sleep apnea will often exhibit a breathing pattern in which the flow of air through an airway is partially occluded. This means that at least one portion of the airway is not fully open. Although air flows through the airway, the air is constricted as it passes through the partially occluded airway. The sound of air as it passes through a partially occluded airway differs from the sound of air as it passes through a fully open airway. That is, the sound of partially occluded breathing has different sound characteristics than the sound of normal breathing.

When person 120 begins to exhibit a breathing pattern in which the flow of air is partially occluded, then controller 230 receives microphone signals that are indicative of partially occluded breathing. The signal pattern that results from the digital signal processing analysis of the "partially occluded breathing" microphone signals is stored in memory unit 260 as a "partially occluded breathing" signal pattern. Controller 230 is capable of recalling the "partially occluded breathing" signal pattern from memory unit 260 in order to compare other signal patterns with the "partially occluded breathing" signal pattern.

While person 120 is breathing, controller 230 is capable of monitoring the microphone signals that are representative of the breathing sounds. Controller 230 is also capable of obtaining the signal patterns that result from the digital signal processing analysis of the microphone signals. Controller 230 is also capable of comparing the current signal patterns with the. "partially occluded breathing" signal pattern. When controller 230 determines that a current signal pattern is substantially the same as the "partially occluded breathing" signal pattern, then controller 230 sends an alarm signal to base station 310. The alarm signal indicates that at least one signal pattern has been identified that is associated with a partially occluded breathing pattern.

At the onset of an obstructive sleep apnea event, a person may exhibit a breathing pattern in which the flow of air through an airway differs from normal breathing. In such cases, the sound of air as it passes through the airway at the onset of an obstructive sleep apnea event differs from the sound of air as it passes through a fully open airway. That is, the sound of breathing at the onset of an obstructive sleep apnea event has different sound characteristics than the sound of normal breathing.

When person 120 begins to exhibit a breathing pattern associated with the onset of an obstructive sleep apnea event, then controller 230 receives microphone signals that are indicative of "apnea onset breathing." The signal pattern that results from the digital signal processing analysis of the "apnea onset breathing" microphone signals is stored in memory unit 260 as an "apnea onset breathing" signal pattern. Controller 230 is capable of recalling the "apnea onset breathing" signal pattern from memory unit 260 in order to compare other signal patterns with the "apnea onset breathing" signal pattern.

While person 120 is breathing, controller 230 is capable of monitoring the microphone signals that are representative of the breathing sounds. Controller 230 is also capable of obtaining the signal patterns that result from the digital signal processing analysis of the microphone signals. Controller 230 is also capable of comparing the current signal patterns with the "apnea onset breathing" signal pattern. When controller 230 determines that a current signal pattern is substantially the same as the "apnea onset breathing" signal pattern, then controller 230 sends an alarm signal to base station 310. The alarm signal indicates that at least one signal pattern has been identified that is associated with a breathing pattern that occurs at the onset of an obstructive sleep apnea event.

After controller 230 signals that person 120 is exhibiting a breathing pattern that is associated with the onset of an obstructive sleep apnea event, steps may be taken to stimulate the body of person 120 in a manner that will terminate the obstructive sleep apnea event before cessation of breathing occurs.

As previously described, controller 230 may receive an airflow detection signal from airflow sensor 155. Controller 230 is capable of determining from the airflow detection signal when person 120 is inhaling and exhaling. Controller 230 is also capable of determining from the microphone signals when person 120 is inhaling and exhaling. In an alternate advantageous embodiment of the present invention, controller 230 shuts down and ceases monitoring the signal patterns 1) during exhalation, or 2) during inhalation. By operating only during one half of the respiratory cycle, controller 230 uses only one half of the power that would otherwise be required.

If the onset of obstructive sleep apnea fully develops, then cessation of breathing will occur. When person 120 ceases to breathe, then microphones 125, 130, 135, and 140, detect no breathing sounds. When controller 230 receives signals that indicate that a "no breathing" condition has occurred, then controller 230 sends a "no breathing" alarm as previously described.

Figure 5:
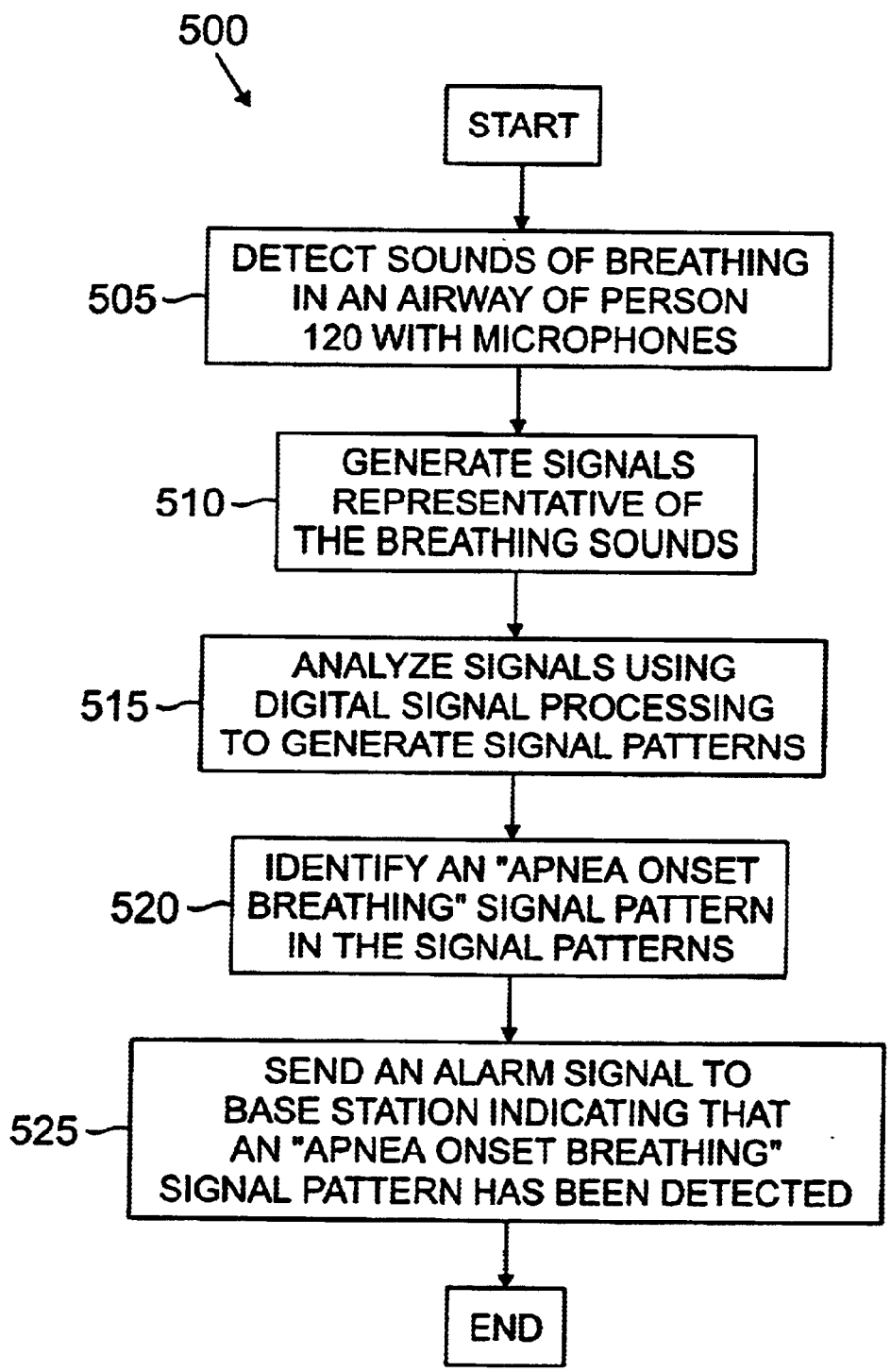
FIG. 5 is a flow diagram illustrating an advantageous embodiment of the method of the present invention.

FIG. 5 illustrates a flow chart 500 depicting the operation of one advantageous embodiment of the present invention. First, microphones 125, 130, 135, and 140, detect sounds of breathing in an airway of person 120 (process step 505) and generate signals that are representative of the breathing sounds (process step 510). Controller 230 then analyzes the signals using digital signal processing software (e.g., Fast Fourier Transform analysis software) to generate signal patterns that are representative of the signals (process step 515).

Controller 230 monitors the signal patterns to identify a signal pattern that is associated with a breathing pattern that occurs at the onset of an obstructive sleep apnea event (process step 520). Controller 230 then sends an alarm to base station 310 that indicates that controller 230 has detected a signal pattern that is associated with a breathing pattern that occurs at the onset of an obstructive sleep apnea event (process step 525).

Although the present invention has been described in detail, those skilled in the art should understand that they can make various changes, substitutions and alterations without departing from the spirit and scope of the invention in its broadest form.

What is claimed is:

1. An apparatus for detecting the onset of an obstructive sleep apnea event before cessation of breathing occurs, said apparatus comprising:

at least one microphone adapted to be acoustically associated with a person, wherein said microphone detects breathing sounds within an airway of said person and generates signals representative of said breathing sounds; and a controller coupled to said at least one microphone that receives said signals, wherein said controller identifies within said signals at least one signal pattern that is associated with a breathing pattern of said person that occurs at the onset of an obstructive sleep apnea event before cessation of breathing occurs;

wherein said controller comprises software that analyzes said signals to identify within said signals at least one signal pattern that is associated with a breathing pattern of said person that occurs at the onset of an obstructive sleep apnea event before cessation of breathing occurs wherein said software analyzes said signals using Fast Fourier Transform analysis.

2. The apparatus as claimed in claim 1 further comprising a base station coupled to said controller wherein said controller sends an alarm signal to said base station to indicate that at least one signal pattern has been identified that is associated with a breathing pattern of said person that occurs at the onset of an obstructive sleep apnea event before cessation of breathing occurs.

3. The apparatus as claimed in claim 1 further comprising at least one filter coupled between said at least one microphone and said controller, wherein said at least one filter filters said signals from said at least one microphone to create filtered signals representative of said breathing sounds, and wherein said controller identifies within said filtered signals at least one signal pattern that is associated with a breathing pattern of said person that occurs at the onset of an obstructive sleep apnea event before cessation of breathing occurs.

4. The apparatus as claimed in claim 3 further comprising a base station coupled to said controller wherein said controller sends an alarm signal to said base station to indicate that at least one signal pattern has been identified that is associated with a breathing pattern of said person that occurs at the onset of an obstructive sleep apnea event before cessation of breathing occurs.

5. The apparatus as claimed in claim 1 further comprising an airflow sensor that detects a flow of air within an airway of said person and generates an airflow detection signal that is representative of the presence of said flow of air; and wherein said controller is coupled to said airflow sensor and receives said airflow detection signal from said airflow sensor to obtain information concerning the breathing of said person.

6. An apparatus for detecting the onset of an obstructive sleep apnea event before cessation of breathing occurs, said apparatus comprising:

at least one microphone adapted to be acoustically associated with a person, wherein said microphone detects breathing sounds within an airway of said person and generates signals representative of said breathing sounds; and a controller coupled to said at least one microphone that receives said signals, wherein said controller identifies within said signals at least one signal pattern that is associated with a breathing pattern of said person that occurs at the onset of an obstructive sleep apnea event before cessation of breathing occurs;

wherein said controller only operates during one half of the respiration cycle.

7. The apparatus as claimed in claim 6 wherein said software analyzes said signals using Fast Fourier Transform analysis.

8. An apparatus for detecting the onset of an obstructive sleep apnea event before cessation of breathing occurs, said apparatus comprising:

at least one microphone adapted to be acoustically associated with a person, wherein said microphone detects breathing sounds within an airway of said person and generates signals representative of said breathing sounds; and a controller coupled to said at least one microphone that receives said signals, wherein said controller identifies within said signals at least one signal pattern that is associated with a partially occluded breathing pattern of said person;

wherein said controller comprises software that analyzes said signals to identify within said signals at least one signal pattern that is associated with a partially occluded breathing pattern of said person and wherein said software analyzes said signals using Fast Fourier Transform analysis.

9. The apparatus as claimed in claim 8 further comprising a base station coupled to said controller wherein said controller sends an alarm signal to said base station to indicate that at least one signal pattern has been identified that is associated with a partially occluded breathing pattern of said person.

10. The apparatus as claimed in claim 8 further comprising at least one filter coupled between said at least one microphone and said controller, wherein said at least one filter filters said signals from said at least one microphone to create filtered signals representative of said breathing sounds, and wherein said controller identifies within said filtered signals at least one signal pattern that is associated with a partially occluded breathing pattern of said person.

11. The apparatus as claimed in claim 10 further comprising a base station coupled to said controller wherein said controller sends an alarm signal to said base station to indicate that at least one signal pattern has been identified that is associated with a partially occluded breathing pattern of said person.

12. The apparatus as claimed in claim 8 further comprising an airflow sensor that detects a flow of air within an airway of said person and generates an airflow detection signal that is representative of the presence of said flow of air; and wherein said controller is coupled to said airflow sensor and receives said airflow detection signal from said airflow sensor to obtain information concerning the breathing of said person.

13. An apparatus for detecting the onset of an obstructive sleep apnea event before cessation of breathing occurs, said apparatus comprising:

at least one microphone adapted to be acoustically associated with a person, wherein said microphone detects breathing sounds within an airway of said person and generates signals representative of said breathing sounds; and a controller coupled to said at least one microphone that receives said signals, wherein said controller identifies within said signals at least one signal pattern that is associated with a partially occluded breathing pattern of said person;

wherein said controller only operates during one half of the respiration cycle.

14. The apparatus as claimed in claim 13 wherein said software analyzes said signals using Fast Fourier Transform analysis.

15. A method for detecting the onset of an obstructive sleep apnea event before cessation of breathing occurs, said method comprising the steps of:

detecting breathing sounds within an airway of a person;

generating signals representative of said breathing sounds;

analyzing said signals using Fast Fourier Transform analysis; and identifying within said signals at least one signal pattern that is associated with a breathing pattern of said person that occurs at the onset of an obstructive sleep apnea event before cessation of breathing occurs.

16. The method as claimed in claim 15 further comprising the step of: sending an alarm signal that indicates that at least one signal pattern has been identified that is associated with a breathing pattern of said person that occurs at the onset of an obstructive sleep apnea event before cessation of breathing occurs.

17. The method as claimed in claim 15 further comprising the steps of:

filtering said signals representative of said breathing sounds to create filtered signals representative of said breathing sounds;

analyzing said filtered signals using Fast Fourier Transform analysis; and identifying within said filtered signals at least one signal pattern that is associated with a breathing pattern of said person that occurs at the onset of an obstructive sleep apnea event before cessation of breathing occurs.

18. The method as claimed in claim 17 further comprising the step of:

sending an alarm signal that indicates that at least one signal pattern has been identified that is associated with a breathing pattern of said person that occurs at the onset of an obstructive sleep apnea event before cessation of breathing occurs.

19. The method as claimed in claim 15 further comprising the steps of:

recording said at least one signal pattern that is associated with a breathing pattern of said person that occurs at the onset of an obstructive sleep apnea event before cessation of breathing occurs;

monitoring said signals representative of said breathing sounds as said person breathes;

comparing said signals representative of said breathing sounds with said recorded at least one signal pattern that is associated with a breathing pattern of said person that occurs at the onset of an obstructive sleep apnea event before cessation of breathing occurs; and identifying within said signals a signal pattern that is substantially the same as said recorded at least one signal pattern that is associated with a breathing pattern of said person that occurs at the onset of an obstructive sleep apnea event before cessation of breathing occurs.

20. The method as claimed in claim 19 further comprising the step of:

sending an alarm signal that indicates that at least one signal pattern has been identified that is associated with a breathing pattern of said person that occurs at the onset of an obstructive sleep apnea event before cessation of breathing occurs.

21. The method as claimed in claim 15 further comprising the step of:

recording said at least one signal pattern that is associated with a breathing pattern of said person that occurs at the onset of an obstructive sleep apnea event before cessation of breathing occurs.

22. A method for detecting the onset of an obstructive sleep apnea event before cessation of breathing occurs, said method comprising the steps of:

detecting breathing sounds within an airway of a person;

generating signals representative of said breathing sounds;

identifying within said signals at least one signal pattern that is associated with a breathing pattern of said person that occurs at the onset of an obstructive sleep apnea event before cessation of breathing occurs; and detecting breathing sounds within said airway of said person only during one half of the respiration cycle.

23. A method for detecting the onset of an obstructive sleep apnea event before cessation of breathing occurs, said method comprising the steps of:

detecting breathing sounds within an airway of a person;

generating signals representative of said breathing sounds;

analyzing said signals using Fast Fourier Transform analysis;

identifying within said signals at least one signal pattern that is associated with a partially occluded breathing pattern of said person;

recording said at least one signal pattern that is associated with a partially occluded breathing pattern of said person;

monitoring said signals representative of said breathing sounds as said person breathes;

comparing said signals representative of said breathing sounds with said recorded at least one signal pattern that is associated with a partially occluded breathing pattern of said person; and identifying within said signals a signal pattern that is substantially the same as said recorded at least one signal pattern that is associated with a partially occluded breathing pattern of said person.

24. The method as claimed in claim 23 further comprising the step of:

sending an alarm signal that indicates that at least one signal pattern has been identified that is associated with a partially occluded breathing pattern of said person.

25. A method for detecting the onset of an obstructive sleep apnea event before cessation of breathing occurs, said method comprising the steps of:

detecting breathing sounds within an airway of a person;

generating signals representative of said breathing sounds;

analyzing said signals using Fast Fourier Transform analysis; and identifying within said signals at least one signal pattern that is associated with a normal breathing pattern of said person;

recording said at least one signal pattern that is associated with a normal breathing pattern of said person;

monitoring said signals representative of said breathing sounds as said person breathes;

comparing said signals representative of said breathing sounds with said recorded at least one signal pattern that is associated with a normal breathing pattern of said person; and identifying within said signals a signal pattern that is substantially different from said recorded at least one signal pattern that is associated with a normal breathing pattern of said person.

* * * * *

UNITED STATES PATENT AND TRADEMARK OFFICE
CERTIFICATE OF CORRECTION

PATENT NO. : 6,666,830 B1
DATED : December 23, 2003
INVENTOR(S) : Michael L. Lehrman and Michael E. Halleck It is certified that error appears in the above-identified patent and that said Letters Patent is hereby corrected as shown below:

Column 10,
Line 62, delete Claim 7 and replace with -- The apparatus as claimed in Claim 6 wherein said controller comprises software that analyzes said signals using Fast Fourier Transform analysis. --

Column 11,
Line 62, delete Claim 14 and replace with -- The apparatus as claimed in Claim 13 wherein said controller comprises software that analyzes said signals using Fast Fourier Transform analysis. --

Signed and Sealed this

Fifth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,666,830 B1
DATED : December 23, 2003
INVENTOR(S) : Lehrman et al.

It is certified that error appears in the above-identified patent and that said Letters Patent is hereby corrected as shown below:

Title page,
Item [73], Assignee, replace "East River Ventures, LP New York NY (US)" with
-- iLife Solutions, Inc. Dallas, TX (US) --.

Signed and Sealed this

Fifteenth Day of November, 2005

JON W. DUDAS
*Director of the United States Patent and Trademark Office*